United States Patent [19]

Cousens et al.

[11] Patent Number: 5,342,921
[45] Date of Patent: Aug. 30, 1994

[54] SUPEROXIDE DISMUTASE FUSION POLYPEPTIDES FOR EXPRESSION OF MAMMALIAN PROTEINS

[75] Inventors: Lawrence S. Cousens; Patricia A. Tekamp-Olson, both of San Francisco; Jeffrey R. Shuster, Walnut Creek; James P. Merryweather, Berkeley, all of Calif.

[73] Assignee: Chiron Corporation, Emeryville, Calif.

[21] Appl. No.: 680,046

[22] Filed: Mar. 29, 1991

Related U.S. Application Data

[60] Continuation of Ser. No. 169,833, Mar. 17, 1988, abandoned, which is a division of Ser. No. 845,737, Mar. 28, 1986, Pat. No. 4,751,180, which is a continuation-in-part of Ser. No. 717,209, Mar. 28, 1985, abandoned.

[51] Int. Cl.$^5$ ............. C07K 3/00; C07K 13/00
[52] U.S. Cl. .................. 530/324; 530/303; 530/304; 530/350; 530/399; 435/244; 435/814; 435/69.9; 435/183
[58] Field of Search ........... 530/303, 304, 324, 350; 435/244, 814, 69.9, 183

[56] References Cited

U.S. PATENT DOCUMENTS 4,366,246 12/1982 Riggs .
4,469,631 9/1984 Baxter et al. .
4,751,180 6/1988 Cousens ............... 435/69.7

FOREIGN PATENT DOCUMENTS

27461/84 11/1984 Australia .
0089626 9/1983 European Pat. Off. .
109560 5/1984 European Pat. Off. .
0123228 10/1984 European Pat. Off. .
95361 11/1984 European Pat. Off. .
0131363 1/1985 European Pat. Off. .
164556 12/1985 European Pat. Off. .
0138111B1 11/1991 European Pat. Off. .
WO8403103 8/1984 PCT Int'l Appl. .

OTHER PUBLICATIONS

Ratner, *Biotechnology*, 7(11), 1129–1133, Nov. 1989.
Tuite et al. (1982) *Embo J*, 1(5):603–608.
Sherman et al. (1983) *Proc. Natl. Acad. Sci. U.S.A.*, 80:5465–5469.
Hallewell, R. A., et al., *Proc. Natl. Sci.*, (1985) 13:2017–34.
Villa-Komaroff et al., *Proc. Nat'l. Acad. Sci. USA* (1978) 75:3727–3731.
Paul et al., *European J. Cell Biol.* (1983) 31:171–174.
Goeddel et al., *Proc. Nat'l. Acad. Sci. USA* (1979).
Stepien et al., *Gene* (1983) 24:289–297.
Lieman-Hurwitz et al., (1982) *Proc. Natl. Acad. Sci. USA* 79:2808–2811.

*Primary Examiner*—F. T. Moezie
*Attorney, Agent, or Firm*—Grant D. Green

[57] ABSTRACT

Novel methods and compositions are provided for enhanced yield of heterologous proteins in fungi. The method and compositions involve employing fusion sequences involving a sequence encoding a heterologous product produced in relatively large amount as a stable polypeptide in the host fused to a second sequence in open reading frame with the prior sequence coding for a different heterologous polypeptide, where the two polypeptides are joined by a selectively cleavable linkage. In particular, a sequence coding for superoxide dismutase is joined to another polypeptide of interest at either terminus of the superoxide dismutase in a yeast expression vector under transcriptional control of an active promoter and the vector introduced into a yeast host and the host grown. High yields of the fusion product are obtained in this manner, where the fusion product can be selectively cleaved so as to produce both the superoxide dismutase and the other polypeptide in high yield.

The S. cerevisiae strain 2150-2-3 (pYASI1) was deposited at the A.T.C.C. on Feb. 27, 1985 and given accession no. 20745.

The S. cerevisiae strain AB110 (pYLUIGF2-14) was deposited at the A.T.C.C. on Mar. 19, 1986 and given accession no. 20796.

9 Claims, No Drawings

SUPEROXIDE DISMUTASE FUSION POLYPEPTIDES FOR EXPRESSION OF MAMMALIAN PROTEINS

CROSS REFERENCE TO RELATED APPLICATIONS

The application is a continuation of Ser. No 07/169,833, filed Mar. 17, 1988 now abandoned which is a division of Ser. No. 06/845,737, filed Mar. 28, 1986, now U.S. Pat. No. 4,751,180, which is a CIP of Ser. No. 06/717,209, filed Mar. 28, 1985, now abandoned.

BACKGROUND OF THE INVENTION

1. Field of the Invention

There are an increasingly large number of genes available for expression, where the expression product may find commercial use. In many instances, the initial expression has been observed in *E. coli*. Expression in *E. coli* has many disadvantages, one in particular being the presence of an enterotoxin which may contaminate the product and make it unfit for administration to mammals. Furthermore, there has not previously been an extensive technology concerned with the production of products in *E. coli*, as compared to such other microorganisms as *Bacillus subtills, Streptomyces,* or yeast, such as *Saccharomyces*.

In many situations, for reasons which have not been resolved, heterologous products, despite active promoters and high copy number plasmids, are produced in only minor amount, if at all, in a microorganism host. Since the economics of the processes are dependent upon a substantial proportion of the nutrients being employed in the expression of the desired product, the production of these products in unicellular microorganisms appears to be unpromising. There is, therefore, a substantial need for processes and systems which greatly enhance the production of a desired polypeptide without substantial detriment to the viability and growth characteristics of the host.

2. Description of the Prior Art

Villa-Komaroff et al., *Proc. Natl. Acad. Sci. USA* (1978) 75:3727–3731, describe a fusion sequence encoding proinsulin joined to the N-terminus of penicillinase for expression in *E. coli*. Paul et al., *European J. Cell Biol.* (1983) 31:171–174, describe a fusion sequence encoding proinsulin joined to the COOHterminus of a portion of the tryptophan E gene product for expression in *E. coli*. Goeddel et al., ibid. (1979) 76:106–110, describe synthetic genes for human insulin A and B chains fused to *E. coli* β-galactosidase gene to provide a fused polypeptide in *E. coli*. Stepien et al., *Gene* (1983) 24:289–297, describe expression of insulin as a fused product in yeast, where the proinsulin gene was fused to the N-terminus coding sequence of GAL1 for expression in yeast.

SUMMARY OF THE INVENTION

Methods and compositions are provided for producing heterologous polypeptides in high yield in a eukaryotic or prokaryotic microorganism host, whereby a completely heterologous fused product is expressed, one part of the peptide being a product shown to be expressed independently in high yield in such host and the remaining part of the product being a polypeptide of interest, resulting in production of the fused product in high yield. Sequences coding for the two polypeptides are fused in open reading frame, where the high yield polypeptide encoding sequence may be at either the 5'- or 3'-terminus. The two polypeptides contained in the expression product may be joined by a selectively cleavable link, so that the two polypeptides may be separated to provide for high yield of each of the polypeptides. Alternatively, the cleavage site may be absent if cleavage of the fused protein is not required for its intended use. Particularly, a yeast host is employed where the high yield polypeptide is superoxide dismutase (SOD).

DESCRIPTION OF THE SPECIFIC EMBODIMENTS

Novel methods and compositions are provided for enhancing the production of heterologous products in eukaryotic organisms, particularly yeast or prokaryotic organisms, such as *E. coli*, by employing sequences encoding for a polypeptide, which is a combination of two polypeptide regions joined by a selectively cleavable site. The two regions are a first region which is a polypeptide produced independently in high yield in the host and a second polypeptide of independent interest and activity, particularly one which is only difficultly obtained in the host.

Hosts of interest include eukaryotic unicellular microorganisms, particular fungi, such as *Phycomycetes, Ascomycetes, Basidiomycetes* and *Deuteromycetes*, more particularly *Ascomycetes*, such as yeast, e.g., such as *Saccharomyces, Schizosaccharomyces,* and *Kluyveromyces*, etc. Prokaryotic hosts may also be employed such as *E. coli, B. subtilis,* etc.

The stable polypeptide to be used as the first region in the fusion may be determined empirically. Thus, as heterologous polypeptides are developed in various host organisms, the yield of the polypeptide as compared to total protein may be readily determined. As to those polypeptides which are produced in amounts of 5% or greater of the total protein produced by the host, those DNA sequences encoding for such polypeptides may be used in this invention. The DNA sequences may be identical to the heterologous gene encoding the sequence, may be mutants of the heterologous gene, or may have one or more codons substituted, whereby the codons are selected as being preferred codons by the host. Preferred codons are those codons which are found in substantially greater than the mathematical probability of finding such codon, based on the degree of degeneracy of the genetic code, in those proteins which are produced in greatest individual abundance in the host. Particularly, in yeast, the glycolytic enzymes may be the basis for determining the preferred codons.

The entire gene or any portion of the gene may be employed which provides for the desired high yield of polypeptide in the host. Thus, where the stable polypeptide is of lesser economic value than the polypeptide of interest, it may be desirable to truncate the gene to a fragment which still retains the desirable properties of the entire gene and its polypeptide product, while substantially reducing the proportion of the total fused product which is the stabilizing polypeptide. As illustrative of a gene encoding a stable polypeptide product in the yeast, is the gene encoding for superoxide dismutase, more particularly human superoxide dismutase.

The DNA sequences coding for the two polypeptides, the stabilizing polypeptide and the polypeptide of interest, may be obtained in a variety of ways. The sequences encoding for the polypeptide may be derived from natural sources, where the messenger RNA or chromosomal DNA may be identified with appropriate probes, which are complementary to a portion of the coding or non-coding sequence. From messenger RNA, single-stranded (ss) DNA may be prepared employing reverse transcriptase in accordance with conventional techniques. The ss DNA complementary strand may then be used as the template for preparing a second strand to provide double-stranded (ds) cDNA containing the coding region for the polypeptide. Where chromosomal DNA is employed, the region containing the coding region may be detected employing probes, restriction mapped, and by appropriate techniques isolated substantially free of untranslated 5' and 3' regions. Where only portions of the coding sequence are obtained, the remaining portions may be provided by synthesis of adapters which can be ligated to the coding portions and provide for convenient termini for ligation to other sequences providing particular functions or properties.

Where the two genes are obtained in-whole or in-part from naturally occurring sources, it will be necessary to ligate the two genes in proper reading frame. If cleavage of the fused protein is required, where their juncture does not define a selectable cleavage site, genes will be separated by a selectively cleavable site. The selectively cleavable site will depend to some degree on the nature of the genes. That is, the means for cleaving may vary depending upon the amino acid sequence of one or both genes.

Alternatively, there will be situations where cleavage is not necessary and in some situations undesirable. Fused proteins may find use as diagnostic reagents, in affinity columns, as a source for the determination of a sequence, for the production of antibodies using the fused protein as an immunogen, or the like.

The two genes will normally not include introns, since splicing of mRNA is not extensively employed in the eukaryotic unicellular microorganisms of interest.

The polypeptide of interest may be any polypeptide, either naturally occurring or synthetic, derived from prokaryotic or eukaryotic sources. Usually, the polypeptide will have at least 15 amino acids (gene of 45 bp), more usually 30 amino acids (gene of 90 bp), and may be 300 amino acids (gene of 900 bp) or greater.

Polypeptides of interest include enzymes, viral proteins (e.g. proteins from AIDS related virus, such as p18, p25, p31, gp41, etc.), mammalian proteins, such as those involved in regulatory functions, such as lymphokines, growth factors, hormones or hormone precursors (e.g., proinsulin, insulin like growth factors, e.g., IGF-I and -II, etc.), etc., blood clotting factors, clot degrading factors, immunoglobulins, etc. Fragments or fractions of the polypeptides may be employed where such fragments have physiological activity, e.g., immunological activity such as cross-reactivity with the parent protein, physiological activity as an agonist or antagonist, or the like.

One of the methods for selectable cleavage is cyanogen bromide which is described in U.S. Pat. No. 4,366,246. This technique requires the absence of an available methionine other than at the site of cleavage or the ability to selectively distinguish between the methionine to be cleaved and a methionine within the polypeptide sequence. Alternatively, a protease may be employed which recognizes and cleaves at a site identified by a particular type of amino acid. Common proteases include trypsin, chymotrypsin, pepsin, bromelain, papain, or the like. Trypsin is specific for basic amino acids and cleaves on the carboxylic side of the peptide bond for either lysine or arginine. Further, peptidases can be employed which are specific for particular sequences of amino acids, such as those peptidases which are involved in the selective cleavage of secretory leader signals from a polypeptide. These enzymes are specific for such sequences which are found with α-factor and killer toxin in yeast, such as KEX 2 endopeptidase with specificity for pairs of basic residues (Julius et al., Cell (1984) 37:1075–1089). Also, enzymes exist which cleave at specific sequences of amino acids. Bovine enterokinase (Light et al., Anal. Biochem. (1980) 106:199–206) cleaves to the carboxylic side of lysine or arginine that is preceded by acid residues of aspartic acid, glutamic acid, or carboxymethyl cysteine. Particularly useful is the sequence $(Asp)_4$ Lys found naturally as part of the activation peptide of trypsinogen in many species. Other enzymes which recognize and cleave specific sequences include: Collagenase (Germino and Batia, Proc. Natl. Acad. Sci. (1984) 81:4692–4696); factor X (Nagai & Thygersen, Nature (1984) 309:810–812); and polyubiquitin processing enzyme (Ozakaynak et al., Nature (1984) 312:663–666).

In addition to the amino acids comprising the cleavable site, it may be advantageous to separate further the two fused polypeptides. Such a "hinge" would allow for steric flexibility so that the fused polypeptides would be less likely to interfere with each other, thus preventing incorrect folding, blockage of the cleavage site, or the like.

The "hinge" amino acid sequence could be of variable length and may contain any amino acid side chains so long as the side chains do not interfere with the mode of action employed to break at the cleavable site or with required interactions in either fused polypeptide, such as ionic, hydrophobic, or hydrogen bonding. Preferably the amino acids comprising the hinge would have side chains that are neutral and either polar or nonpolar and may include one or more prolines. The hinge region will have at least one amino acid and may have 20 or more amino acids, usually not more than 15 amino acids, particularly the nonpolar amino acids G, A, P, V, I, L, and the neutral polar amino acids, N, Q, S, and T.

Exemplary hinge sequences may be, but are not limited to: N-S; Q-A; N-S-G-S-P; A-A-S-T-P; N-S-G-P-T-P-P-S-P-G-S-P; S-S-P-G-A; and the like. It is contemplated that such hinge sequences may be employed as repeat units to increase further the separation between the fused polypeptides.

So that the "hinge" amino acids are not bound to the final cleaved polypeptide of interest, it is desirable, but not required to practice the invention, to place the "hinge" between the polypeptide that is produced independently at high yield and the sequence for the cleavable site.

Where one or more amino acids are involved in the cleavage site, the codons coding for such sequence may be prepared synthetically and ligated to the sequences coding for the polypeptides so as to provide for a fused protein where all the codons are in the proper reading frame and the selectable cleavage site joins the two polypeptides.

Instead of only a small portion of the fused coding sequence being synthetically prepared, the entire sequence may be synthetically prepared. This allows for certain flexibilities in the choice of codons, whereby one can provide for preferred codons, restriction sites, avoid or provide for particular internal structures of the DNA and messenger RNA, and the like.

While for the most part, the fused coding sequence will be prepared as a single entity, it should be appreciated that it may be prepared as various fragments, these fragments joined to various untranslated regions, providing for particular functions and ultimately the coding sequences brought together at a subsequent stage. However, for clarity of presentation, the discussion will be directed primarily to the situation where the coding sequence is prepared as a single entity and then transferred to an expression vector.

The various sequences comprising the parts of the fused coding sequence can be joined by introducing a first fragment into a cloning vector. The resulting clone may then be restricted at a site internal to the coding sequence and an adapter introduced which will replace any lost codons and which has a convenient terminus for joining to the next fragment. The terminus may be cohesive or blunt-ended, depending upon the particular nucleotides involved. After cloning of the combined first fragment and adapter, the vector may be restricted at the restriction site provided by the adapter and the remaining coding sequence of the second fragment introduced into the vector for ligation and cloning. The resulting fused sequence should be flanked by appropriate restriction sites, so that the entire sequence may be easily removed from the cloning vector for transfer to an expression vector.

The expression vector will be selected so as to have an appropriate copy number, as well as providing for stable extrachromosomal maintenance. Alternatively, the vector may contain sequences homologous to the host genomic sequences to allow for integration and amplification. The expression vector will usually have a marker which allows for selection in the expression host. In order to avoid the use of biocides, which may find use in certain situations, desirably, complementation will be employed, whereby the host will be an auxotroph and the marker will provide for prototrophy. Alternatively, the episomal element may provide for a selective advantage, by providing the host with an enhanced ability to utilize an essential nutrient or metabolite in short supply. The significant factor is that desirably the extrachromosomal cloning vector will provide a selective advantage for the host containing the vector as compared to those hosts which may spontaneously lose the vector during production of the fused polypeptide.

The cloning vector will also include an active transcriptional initiation regulatory region, which does not seriously interfere with the viability of the host. Regions of particular interest will be associated with the expression of enzymes involved in glycolysis; acid phosphatase; heat shock proteins; metallothionein; etc. Enzymes involved with glycolysis include alcohol dehydrogenase, glyceraldehyde-3phosphate dehydrogenase, glucose-6-phosphate dehydrogenase, pyruvate kinase, triose phosphate isomerase, phosphofructokinase, etc.

Various transcriptional regulatory regions may be employed involving only the region associated with RNA polymerase binding and transcriptional initiation ("promoter region"), two of such regions in tandem, or a transcriptional initiation regulatory region ("control region"), normally 5'- to the promoter region, where the control region may be normally associated with the promoter or with a different promoter in the wild-type host. The control region will provide for inducible regulation where induction may be as a result of a physical change, e.g. temperature, or chemical change, e.g. change in nutrient or metabolite concentration, such as glucose or tryptophan, or change in pH or ionic strength.

Of particular interest is the use of hybrid transcriptional initiation regulatory regions. Preferably, the hybrid transcriptional initiation regulatory region will employ a glycolytic enzyme promoter region. The control region may come from the control regions of a variety of expression products of the host, such as ADHII, GAL4, PHO5, or the like.

The transcriptional initiation regulatory regions may range from about 50–1000 base pairs (bp) of the region 5' of the wild-type gene. In addition to regions involved with binding of RNA polymerase, other regulatory signals may also be present, such as a capping sequence, transcriptional initiation sequences, enhancer, transcriptional regulatory region for inducible transcription, and the like.

The transcriptional initiation regulatory region will normally be separated from the terminator region by a polylinker, which has a plurality of unique restriction sites, usually at least two, and not more than about 10, usually not more than about six. The polylinker will generally be from about 10–50bp. The polylinker will be followed by the terminator region, which may be obtained from the same wild-type gene from which the promoter region was obtained or a different wild-type gene, so long as efficient transcription initiation and termination is achieved when the two regions are used.

By digestion of the expression vector with the appropriate restriction enzymes, the polylinker will be cleaved and the open reading frame sequence coding for the fused polypeptide may be inserted. Where the polylinker allows for distinguishable termini, the fused gene can be inserted in a single orientation, while where the termini are the same, insertion of the fused gene will result in plasmids having two different orientations, only one of which will be the proper orientation. In any event, the expression vector may be cloned where it has a prokaryotic replication system for isolation and purification and then introduced into an appropriate eukaryotic host, such as a yeast host. Introduction of foreign DNA into eukaryotic hosts can be performed in a wide variety of ways, such as calcium-polyethylene glycol treated DNA with spheroplasts, use of liposomes, mating, or the like.

The host cells containing the plasmid with the fused gene capable of expression are then grown in an appropriate nutrient medium for the host. Where an inducible transcriptional initiation regulatory region is employed, the host cell may be grown to high density and initiation turned on for expression of the fused polypeptide. Where the promoter is not inducible, then constitutive production of the desired fused polypeptide will occur.

The cells may be grown until there is no further increase in product formation or the ratio of nutrients consumed to product formation falls below a predetermined value, at which time the cells may be harvested, lysed and the fused protein obtained and purified in accordance with conventional techniques. These techniques include chromatography, e.g., HPLC; electrophoresis; extraction; density gradient centrifugation, or the like. Once the fused protein is obtained, it will then be selectively cleaved in accordance with the nature of the selectively cleavable linkage. This has been described previously in relation to the description of the various linkages.

In some instances a secretory leader and processing signal may be included as part of the fused polypeptide. Various secretory leader and processing signals are known, such as yeast s-factor, yeast killer toxin and the like. The DNA sequence coding for these polypeptide signals may be linked in proper reading frame to the 5'-end (in direction of transcription of the sense strand) of the DNA sequence coding for the fused polypeptide to provide for transcription and translation of a pre-fused polypeptide.

In accordance with the subject invention, the product is produced in at least a 5 weight percent, preferably at least 6 weight percent, and more preferably at least about 10 weight percent, of the total protein of the host. In this manner, the nutrients employed are efficiently utilized for conversion to a desired product.

The following examples are offered by way of illustration and not by way of limitation.

EXPERIMENTAL

EXAMPLE I: Construction and Expressions of Expression Vectors for SOD-Proinsulin Fusion Protein Construction of pYSI1

A yeast expression plasmid pYSI1, containing the human SOD gene fused to the amino-terminus of human proinsulin gene, under the regulation of the GAP promoter and terminator was constructed. A triplet coding for methionine was included between the SOD and proinsulin genes to allow for chemical processing of the fusion protein. The SOD sequences correspond to a cDNA isolated from a human liver library, except for the first 20 codons which were chemically synthesized. The proinsulin sequence was chemically synthesized according to the amino acid sequence reported by (Bell et al. (1979), Nature 282:525–527), but using yeast preferred codons. The GAP promoter and terminator sequences were obtained from the yeast GAP gene (Holland & Holland, *J. Biol. Chem.* (1979) 254:5466–5474) isolated from a yeast library.

Plasmid pYSI1 was constructed as follows. Three fragments were employed which involve a 454 bp NcoI-Sau3A fragment isolated from phSOD (also designated as pSODNco5), where the fragment includes the entire coding sequence for human superoxide dismutase (hSOD) with the exception of the last three 3'-codons; a 51bp Sau3A-HindIII synthetic adapter, which codes for the last three codons of hSOD, methionine, and the first 14 codons of proinsulin; and a 231bp HindIII-SalI fragment, isolated from pINS5, which encodes proinsulin excepting the first 14 amino acids. These fragments were ligated together and introduced into the plasmid pPGAP, which had been previously digested with NcoI and SalI and alkaline phosphatase treated. The resulting plasmid pSI1 was digested with BamHI to provide an expression cassette which was cloned into plasmid pC1/1 to yield pYSI1.

Plasmid phSOD (also designated as pSODNco5) is a pBR322-derived bacterial expression vector which contains a complete cDNA coding (except that the first 20 codons were chemically synthesized) for hSOD as described in copending application Ser. No. 609,412 filed on May 11, 1984. Plasmid pINS5 is a pBR322-derived vector which contains a proinsulin coding sequence chemically synthesized according to the amino acid sequence reported by Bell et al., *Nature* (1979) 282:525–527. Plasmid pPGAP is a pBR322-derived vector described in copending application 609,412 (supra) which contains a GAP promoter and GAP terminator (Holland and Holland, *J. Biol. Chem.* (1979) 254:5466–5474) with a polylinker between them, which provides for single restriction sites for cloning. Plasmid pC1/1 is a yeast expression vector which includes pBR322 sequences, 2μ plasmid sequences and the yeast gene LEU2 as a selectable marker. Plasmid pC1/1 is a derivative of pjDB219, Beggs, *Nature* (1978) 275:104, in which the region corresponding to bacterial plasmid pMB9 in pJDB219 has been replaced by pBR322 in pC1/1. This mixture was used to transform *E. coli* HB101 cells. Transformants were selected by ampicillin resistance and their plasmids analyzed by restriction endonucleases. DNA from one selected clone (pYEGF-8) was prepared and used to transform yeast AB103 cells. Transformants were selected by their leu+- phenotype.

Construction of pYS12

To prepare the fused gene having the hSOD coding sequence at the 3'-terminus in the direction of transcription separated from the proinsulin gene by a "spacer" of codons coding for K-R-S-T-S-T-S, the following fragments were ligated. A 671bp BamHI-SalI fragment containing the GAP promoter, the proinsulin gene and codons for the spacer amino acids; a 14bp SalI-NcoI synthetic adapter, which codes for the last spacer amino acids as a junction of both genes; and a 1.5 kb NcoI-BamHI fragment isolated from pC1/1 GAPSOD described in copending application 609,412 (supra), which includes the hSOD coding region, 56bp of hSOD terminator and 934bp of GAP terminator region. The resulting cloned fragment was isolated and inserted into BamHI digested, alkaline phosphatase treated pC1/1.

Plasmids pPKI1 and pPKI2

Plasmids homologous to pYSI1 and pYSI2, but using the yeast pyruvate kinase (PYK) gene instead of hSOD gene, were also constructed. pPKI1 contains the PYK coding sequence fused to the amino-terminus of the human proinsulin gene under regulation of the yeast PYK promoter and yeast GAP terminator. pPKI2 contains the PYK coding sequence at the 3'-terminus in the direction of transcription separated from the proinsulin gene by a "spacer" of codons coding for K-R-S-T-S. This fused gene is under regulation of the GAP promoter and PYK terminator.

Construction of pYASI1

This yeast expression plasmid is similar to pYSI1 and contains the hSOD gene fused to the amino terminus of the human proinsulin gene, with a methionine codon at the junction between both genes. The fusion gene is under control of the hybrid inducible ADH2-GAP (yeast alcohol dehydrogenase 2) promoter and the GAP terminator. An about 3kbp BamHI expression cassette was constructed by replacing the GAP promoter sequence from pYSI1 with the hybrid ADH2-GAP promoter sequence.

The ADH2 portion of the promoter was constructed by cutting a plasmid containing the wild type ADH2 gene (plasmid pADR2, see Beier and Young, *Nature* (1982) 300:724–728) with the restriction enzyme EcoR5, which cuts at a position +66 relative to the ATG start codon, as well as in two other sites in pADR2, outside of the ADH2 region. The resulting mixture of a vector fragment and two smaller fragments was resected with Bal31 exonuclease to remove about 300 bp. Synthetic XhoI linkers were ligated onto the Bal31 treated DNA. The resulting DNA linker vector fragment (about 5 kb) was separated from the linkers by column chromatography, cut with the restriction enzyme XhoI, religated and used to transform *E. coli* to ampicillin resistance. The positions of the XhoI linker additions were determined by DNA sequencing. One plasmid which contained an XhoI linker located within the 5' non-transcribed region of the ADH2 gene (position -232 from ATG) was cut with the restriction enzyme XhoI, treated with nuclease S1, and subsequently treated with the restriction enzyme EcoRI to create a linear vector molecule having one blunt end at the site of the XhoI linker and an EcoRI end.

The GAP portion of the promoter was constructed by cutting plasmid pPGAP (supra) with the enzymes BamHI and EcoRI, followed by the isolation of the 0.4 Kbp DNA fragment. The purified fragment was cut with the enzyme AluI to create a blunt end near the BamHI site.

Plasmid pJS104 was constructed by the ligation of the AluI-EcoRI GAP promoter fragment to the ADH2 fragment present on the linear vector described above.

Plasmid pJS104 was digested with BamHI (which cuts upstream of the ADH2 region) and with NcoI (which cuts downstream of the GAP region). The about 1.3 Kbp fragment containing the ADH2-GAP promoter was gel purified and ligated to an about 1.7 Kbp fragment containing the hSOD-proinsulin fusion DNA sequences and GAP terminator present in pYSI1 (previously described). This 3Kbp expression cassette was cloned into BamHI digested and phosphatase treated pC1/1 to yield pYASI1.

Construction of pYASI1 Derivatives Containing Trypsin and Enterokinase Cleavage Sites A series of plasmids were constructed derived from pYASI1, in which the GAP terminator was replaced by the α-factor terminator (Brake et al., *Proc. Natl. Acad. Sci. USA* (1984) 81:4642) and the cleavage site between SOD and proinsulin was modified to code for trypsin or enterokinase processing sites. Sequences coding for Lys-Arg were used to replace the methionine codon in pYASI1 yielding a trypsin site. Alternatively, sequences coding for (Asp)$_4$Lys were used at the cleavage site to yield an enterokinase site. In addition, sequences coding for extra hinge amino acids were also inserted between the SOD and the cleavage site in other constructions.

Expression of Fusion Proteins

Yeast strain 2150-2-3 (*Mat a, ade* 1, *leu* 2–04, cir°) or P017 (*Mat a, leu* 2–04, cir°) were transformed with the different vectors according to Hinnen et al., *Proc. Natl. Acad. Sci. USA* (1978) 75:1929-1933. Single transformant colonies harboring constitutive GAP regulated vectors were grown in 2 ml of leu⁻selective media to late log or stationary phase. Cells harboring inducible ADH2-GAP regulated vectors were grown to saturation in leu ⁻selective media, subsequently diluted 1:20 (v/v) in YEP, 3% ethanol, with or without 2–3.5mM CuSO$_4$ and grown to saturation in this medium. Cells were lysed in the presence of SDS and reducing agent and the lysates clarified by centrifugation. Cleared lysates were subjected to polyacrylamide gel electrophoresis (Laemmli, *Nature* (1970) 277:680). Following staining with Coomassie blue, a band of about 28 kDal (kilodaltons) was observed, the size predicted for the fusion protein. This band was detected in those cells transformed with expression vectors, while being absent from extracts of cells harboring control (pC1/1) plasmids. Amount of protein per band was determined by densitometric analysis of the Coomassie blue stained gels. The fusion protein accounts for over 10% of the total cell protein as estimated from the stained gels in those cells transformed with pYSI1, pYSI2 or pYASI1, while it accounts for less than 0.5% in pYPKI1 or pYPKI2 transformants (See Table 1).

TABLE 1

The Yield of SOD-PI form 2150 or P017 Transformed with Different Expression Plasmids and Grown in the Absence/Presence of 2–3.5 mM CuSO$_4$.

| Strain | Plasmid | Description of sequences contained in the expression cassette. | Expression (percent of total cell protein)[1] | |
|---|---|---|---|---|
| | | | −Cu$^{++}$ | +Cu$^{++}$ |
| 2150 | pYPKI 1 | PYK$_p$ PYK M BCA5 GAP$_t$ | 0.5 | |
| 2150 | pYPKI 2 | GAP$_p$ M BCA5 KRSTS$_2$ PYK PYK$_t$ | 0.5 | |
| 2150 | pYSI 1 | GAP$_p$ SOD M BCA5 GAP$_t$ | 10 | |
| 2150 | pYSI 2 | GAP$_p$ M BCA5 KR(ST)$_2$S SOD GAP$_t$ | 10 | |
| | | SOD Met Proinsulin | | |
| 2150 | pYASI 1 | (ADH-GAP)$_p$ SOD M BCA5 GAP$_t$ | 10 | |
| P017 | pYASI 1 | (ADH-GAP)$_p$ SOD M BCA5 GAP$_t$ | 20–30 | 20–30 |
| | | SOD (hinge) (Asp)$_4$LysPI | | |
| P017 | pYSI12 | (ADH-GAP)$_p$SOD-D$_4$K-BCA5 α-factor$_t$ | 6–9 | 11–14 |
| P017 | pYSI15 | (ADH-GAP)$_p$SOD-(NS)D$_4$K-BCA5 α-factor$_t$ | 5–6 | 9–14 |
| P017 | pYSI8 | (ADH-GAP)$_p$SOD-(NSGSP)D$_4$K-BCA5 α-factor$_t$ | 5 | 8 |
| P017 | pYSI4 | (ADH-GAP)$_p$SOD-(NSGPTPPSPGSP)D$_4$K-BCA5 α-factor$_t$ | 9–12 | 9–16 |
| | | SOD (hinge) LysArgPI | | |
| P017 | pYSI13 | (ADH-GAP)$_p$SOD-KR-BCA5 α-factor$_t$ | 8–10 | 8–10 |
| P017 | pYSI10 | (ADH-GAP)$_p$SOD-(NSGSP)KR-BCA5 α-factor$_t$ | 5–7 | 10–15 |

TABLE 1-continued

The Yield of SOD-PI form 2150 or P017 Transformed with Different
Expression Plasmids and Grown in the Absence/Presence of 2-3.5 mM CuSO$_4$.

| Strain | Plasmid | Description of sequences contained in the expression cassette. | Expression (percent of total cell protein)[1] | |
|---|---|---|---|---|
| | | | −Cu$^{++}$ | +Cu$^{++}$ |
| P017 | pYSI3 | (ADH-GAP)$_p$SOD-(NSGPTPPSPGSP)KR-BCA5 α-factor$_t$ | 5–8 | 15–30 |

[1]Determined by scanning densitometer analysis of Coomassie Blue stained gels.
Note:
Proinsulin (PI) accounts for less than 0.1% of total cell protein in cells transformed with pYGAPINS5, a plasmid containing the proinsulin gene under regulation of GAPDH promoter and terminator (GAP$_p$ M BCA5 GAP$_t$).
PYK: pyruvate kinase gene
SOD: human SOD gene
BCA5: proinsulin gene
P, G, D, N, M, K, R, S, T: one letter amino acid code
GAP$_p$: GAP promoter
GAP$_t$: GAP terminator
PYK$_p$: PYK promoter
PYK$_t$: PYK terminator
(ADH2-GAP)$_p$: hybrid ADH2-GAP promoter
α-factor$_t$: α-factor terminator Results shown in Table 1 indicate that while expression levels of PYK-proinsulin fusion are comparable to those obtained with proinsulin alone (about 0.5% and 0.1%, respectively), the expression levels of hSOD-proinsulin are about 20 to 100 fold higher. The inducible ADH2-GAP hybrid transcriptional initiation regulatory region is preferred, since it is noted that constitutive production in scaled-up cultures results in unstable expression.

The hSOD-proinsulin proteins synthesized by yeast were also submitted to Western analysis. Cleared yeast lysates prepared as described above were electrophoresed on polyacrylamide gels (Laemmli, supra) and proteins were subsequently electroblotted onto nitrocellulose filters (Towbin et al., Proc. Natl. Acad. Sci. USA (1979) 76:3450). Two identical filters were blotted. The filters were preincubated for 1 hr with 1% BSA in PBS and subsequently treated with rabbit anti-hSOD or guinea pig anti-insulin antibodies for 12 hr at 4° C. Both sera had been preadsorbed with pC1/1 control lysate in 10% goat serum. The filters were washed with 1% BSA PBS and a second goat anti-rabbit or anti-guinea pig antibody conjugated with horseradish peroxidase added. Finally, the filters were incubated with horseradish peroxidase color development reagent (Bio-Rad) and washed. The Western analysis showed that the fusion protein reacted with both antibodies.

Cleavage of the Fusion Proteins

A saturated culture of 2150 (pYASI1) was grown in SDC minus leucine plus threonine and adenine, containing 2% glucose. This was used to inoculate a 10 liter fermentor containing YEP with 3% ethanol as carbon source. After 48 hrs at 30° C., the cells were harvested by centrifugation (Sharples), weighed (124 g), and washed with cold water.

The cells were lysed by glass bead disruption (Dyno mill) using a buffer containing 10 mM Tris Cl, pH 7.0, 1 mM EDTA, μg/ml pepstatin A and 1mM PMSF. The mixture was centrifuged for 20 min at 8,000 rpm in a JA10 rotor (Beckman). The pellet was resuspended in 100 mls of buffer and the liquid was removed from the beads. This was repeated until ~500mls of buffer was used to thoroughly remove all pellet material from the glass beads. The resuspended pellet was centrifuged, and the pellet washed a second time. The pellet was then extracted for 30 min in buffer plus 1% SDS.

The SDS soluble fraction was ion-pair extracted using 500 mls of solvent A (Konigsberg and Henderson, (1983) Meth. in Enz. 91, pp. 254–259), the pellet washed once with solvent A, and once with acetone.

After drying in a vacuum desiccator, the powder was dissolved in 140 mls 100% formic acid. Sixty mls of H$_2$O and 20 g CNBr were added. After 24 hrs at room temperature, in the dark, an additional 20 g CNBr was added, and the reaction continued for 24 hrs. At this time, the material was dialyzed overnight against 4 liters H$_2$O using 2000 MW cutoff tubing (Spectrapor). A second dialysis against 0.1% acetic acid followed. After lyophilization, a powder consisting mostly of SOD-homoserine lactone and proinsulin was obtained, weighing 1.1 g.

This powder was dissolved in a 200 ml solution of 7% urea, 9% sodium sulfite, and 8.1% sodium tetrathionate—2H$_2$O, pH 7.5. After incubation for 3 hrs at 37° C., the S-sulfonate products were dialyzed twice versus 10 mM Tris pH 8.0, and once versus 20 mM TEAB (triethylammonium bicarbonate), pH 7.3.

The S-sulfonates were recovered by lyophilization and dissolved in 240 mls DEAE column buffer (Wetzel et al., Gene (1981) 17:63–71) and loaded onto a 60 ml column. After washing with two column volumes, the proinsulin-S-sulfonate was eluted with a 600 ml gradient of 0 to 0.4 M NaCl in column buffer. Fractions containing proinsulin S-sulfonate were pooled and dialyzed twice against 10 mM Tris, pH 7.5, and once against 1 mM Tris.

The product, ~90% pure proinsulin-S-sulfonate, was shown to migrate as expected on pH 9 gel electrophoresis (Linde et al., Anal. Biochem. (1980) 107:165–176), and has the correct 15N-terminal residues. On analysis, the amino acid composition was very close to that expected, not exactly correct due to the presence of a low level of impurities. The yield was 150 mg.

Preliminary results on renaturation have been obtained with the following procedure. The proinsulin-S-sulfonate can be renatured at pH 10.5, with β-mercaptoethanol (Frank et al. (1981) in Peptides: Synthesis, Structure and Function, Proceedings of the Seventh American Peptide Symposium, Rich and Gross, eds., Pierce Chemical Co., Rockford, IL, pp. 729–738). In preliminary experiments, the yield of correctly renatured proinsulin has been monitored by the production of insulin produced from digestion with trypsin and carboxypeptidase B. The proinsulin - S - SO$_3$ produced by this process appears to renature as well as purified porcine proinsulin - S - SO$_3$. This process has been reported to yield 70% of the expected amount of insulin. The insulin produced in this way has the correct N-terminal 15 residues of each A chain and B chain as determined by amino acid sequencing.

EXAMPLE II: Construction and Expression of Expression Vectors for SOD-p31 Fusion Protein A yeast expression plasmid pC1/1-pSP31-GAP-ADH2, containing the human SOD gene fused to the amino terminus of the endonuclease region (p31) of the pol gene of the AIDS related virus (ARV) (Sanchez-Pescador et al., Science (1985) 227:484) was constructed. Expression of SOD-p31 is non-constitutive and is under regulation of a hybrid ADH-GAP promoter.

Construction of pC1/1-pSP31-GAP-ADH2 Derivative

For the construction of a gene for a fused protein SOD-p31 to be expressed in yeast, a plasmid (pS14/39-2) was used. This plasmid contains the SOD gene fused to the proinsulin gene under the regulation of the ADH-2/GAP promoter in the same manner as pYAS1. The proinsulin gene is located between EcoRI and SalI restriction sites. To substitute the proinsulin gene with the p31 fragment, two oligomers designated ARV-300 and ARV-301, respectively, were synthesized using phosphoramidite chemistry. The sequences generate cohesive ends for EcoRI and NcoI on each side of the molecule when the two oligomers are annealed. ARV-300 and ARV-301 have the sequences:

ARV-300 5' AATTCAGGTGTTGGAGC
              GTCCACAACCTCGGTAC 5' ARV-301

Two µg of pS14/39-2 linearized with EcoRI were ligated to 100 picomoles each of phosphorylated ARV-300 and dephosphoryiated ARV-301 in the presence of ATP and T4 DNA ligase in a final volume of 35 µl. The reaction was carried out at 14° C. for 18 hr. The DNA was further digested with SalI and the fragments were resolved on a 1% low melting point agarose gel and a fragment containing the vector plus the SOD gene (~6.5kb) was purified as described above and resuspended in 50 µl of TE (10mM Tris, 1 mM EDTA, pH 8). Five µl of this preparation were ligated to 5 µl of the p31 fragment (ARV248NL, see below) in 20 µl final volume for 18 hr at 14° C. and 5 µl used to transform competent HB101 cells. The resultant plasmid was called pSP31. Twenty µg of this plasmid were digested with BamHI and a fragment of about 2900 bp was isolated by gel electrophoresis, resuspended in TE and ligated to pC1/1 previously cut with BamHI. This DNA was used to transform HB101 and transformants with the BamHI cassette were obtained. Yeast strain P017 (Mat a, leu2-04, cir°) was transformed with this pC1/1-pSP31-GAP-ADH2 derivative.

Preparation of ARV248NL, the p31 Coding Fragment

The 800 bp ARV248NL fragment codes for numbered amino acids 737 to the end of the pol protein as shown in FIG. 2 of Sanchez-Pescador et al. (supra). The following procedure was used for its preparation.

A 5.2 kb DNA fragment was isolated from a KpnI digest of ARV-2 (9B) (Sanchez-Pescador et al., supra) containing the 3' end of the pol gene, or F-1, env and the 5' end of orf-2, that had been run on a 1% low melting point agarose (Sea-Pack) gel and extracted with phenol at 65° C., precipitated with 100% ethanol and resuspended in TE. Eight µl of this material were further digested with SstI for 1 hr at 37° C. in a final volume of 10 µl. After heat inactivation of the enzyme, 1.25 µl of this digest were ligated to 20 ng of M13mp19 previously cut with KpnI and SstI, in the presence of ATP and in a final volume of 20 µl. The reaction was allowed to proceed for 2 hr at room temperature. Five µl of this mixture were used to transform competent E. coli JM101. Clear plaques were grown and single-stranded DNA was prepared as described in Messing and Vieira, Gene (1982) 19:269–276.

The DNA sequence in the M13 template was altered by site specific mutagenesis to generate a restriction site recognized by NcoI (CCATGG). An oligodeoxynucleotide that substitutes the A for a C at position 3845 (FIG. 1 in Sanchez-Pescador et al., supra) and changes a T for an A at position 3851 was synthesized using solid phase phosphoramidite chemistry. Both of these changes are silent in terms of the amino acid sequence, and the second one was introduced to decrease the stability of the heterologous molecules. The oligomer was named ARV-216 and has the sequence:

5'-TTAAAATCACTTGCCATGGCTCTCCAAT-TACTG and corresponds to the noncoding strand since the M13 derivative template 01100484 is single-stranded and contains the coding strand. The 5' dephosphorylated M13 sequencing primer, 50 mM Tris-HCl pH 8, 20 mM KCl, 7 mM MgCl$_2$ and 0.1 mM EDTA. The polymerization reaction was done in 100 µl containing 50 ng/µl DNA duplex, 150 µM dNTPs, 1 mM ATP, 33 mM Tris-acetate pH 7.8, 66 mM potassium acetate, 10 mM magnesium acetate, 5 mM dithiothreitol (DTT), 12.5 units of T4 polymerase, 100 µg/ml T4 gene 32 protein and 5 units of T4 DNA ligase. The reaction was incubated at 30° C. for 30 min and was stopped by the addition of EDTA and SDS (10 mM and 0.2% respectively, final concentration). Competent JM101 E. coli cells were transformed with 1, 2, and 4 µl of a 1:10 dilution of the polymerization product and plated into YT plates. Plaques were lifted by adsorption to nitrocellulose filters and denatured in 0.2 N NaOH, 1.5 M NaCl, followed by neutralization in 0.5 M Tris-HCl pH 7.3, 3 M NaCl and equilibrated in 6 × SSC. The filters were blotted dry, baked at 80° C. for 2 hr and preannealed at 37° C. in 0.2% SDS, 10×Denhardt's 6×SSC. After 1 hr, $7.5 \times 10^6$ cpm of labelled ARV-216 were added to the filters and incubated for 2 additional hr at 37° C. The filters were washed in 6×SSC at 42° C. for 20 min, blot-dried and used to expose film at −70° C. for 1 hr using an intensifying screen. Strong hybridizing plaques were grown and single-stranded DNA was prepared from them and used as templates for sequencing. Sequencing showed that template 01021785 contains the NcoI site as well as the second substitution mentioned above.

A second oligomer was synthesized to insert sites or SalI and EcoRI immediately after the termination codon of the pol gene (position 4647, FIG. 1, Sanchez-Pescador et al., supra). This oligomer was called ARV-248 and has the sequence:

5'-GGTGTTTTACTAAAGAATTCCGTCGAC-TAATCCTCATCC

Using the template 01020785, site specific mutagenesis was carried out as described above except that the filter wash after the hybridization was done at 65° C. As above, 8 strong hybridizing plaques were grown and single-stranded DNA was sequenced. The sequence of template 01031985 shows that it contains the restriction sites for NcoI, SalI, and EcoRI as intended.

Replicative form (RF) of the M13 01031098 template was prepared by growing 6 clear plaques, each in 1.5 ml of 2×YT (0.5% yeast extract, 0.8% tryptone, 0.5% HaCl, 1.5% agar) at 37° C. for 5 hr. Double-stranded DNA was obtained as described by Maniatis, et al., *Molecular Cloning, a Laboratory Manual*, Cold Spring Harbor, 1982, pooled and resuspended in 100 μl final volume. A 20 μl aliquot of RF was cut with NcoI and SalI in a 40 μl volume of digestion buffer. This fragment was used for p31 expression in yeast. The samples were run on a 1% low melting point agarose (Sea-Pack) gel and the DNAs were visualized by fluorescence with ethidium bromide. The 800 bp band was cut and the DNA was extracted from the gel as mentioned above and resuspended in 10 μl of TE. The fragment was called ARV248NL.

Induction of pC1/1-pSP31-GAP-ADH2

Three different kinds of inductions were tried:

1) P017 colonies were induced in either a 10 ml culture of YEP/1% glucose or a leu−/3% ethanol culture for 24 hr. The yeast pellets from each mixture were analyzed for p31 by both polyacrylamide gels and westerns using sera from AIDS patients. Even though the Coomassie-stained gel showed a negative result, in both causes the Western did light up a band of the correct molecular weight.

2) P017 colonies were induced in a 30 ml culture of YEP/1% ethanol for 48 hr. Aliquots were analyzed by PAGE at various time points during the induction. The Coomassie-stained gel shows a band in the correct molecular weight range (47-50 kd) that appears after 14 hr in YEP/1% ethanol and reaches a maximum intensity at 24 hr of induction. The Western result for SOD p31 using sera from AIDS patients correlates well with the Coomassie-stained gel, showing strong bands at 24 and 48 hr of induction.

Purification and Characterization of SOD-p31 from Yeast

Frozen yeast (bacteria) cells were thawed at room temperature and suspended in 1.5 volumes of lysis buffer (20 mM Tris-Cl, pH 8.0, 2 mM EDTA, 1 mM phenylmethylsulfonyl fluoride (PMSF), for bacteria; 50 mM Tris-Cl, pH 8.0, 2 mM EDTA, 1 mM PMSF for yeast), and mixed with 1 volume of acid-washed glass beads.

Cells were broken for 15 min. in a non-continuous mode using the glass chamber of a Dynomill unit at 3,000 rpm, connected to a −20° C. cooling unit. Glass beads were decanted for 2-3 min. on ice, and the cell lysate removed. The decanted glass beads were washed twice with 30 ml of lysis buffer at 4° C. The cell lysate was centrifuged at 39,000×g for 30 min.

The pellet obtained from the above centrifugation was washed once with lysis buffer, after vortexing and suspending it at 4° C. (same centrifugation as above). The washed pellet was treated with 0.2% SDS (for bacteria) and 0.1% SDS (for yeast) in lysis buffer and was agitated by rocking at 4° C. for 10 min. The lysate was centrifuged at 39,000×g for 30 min. The pellet was boiled in sample buffer (67.5 mM Tris-Cl, pH 7.0, 5% β-mercaptoethanol, 2.3% SDS) for 10 min and centrifuged for 10 min. at 39,000×g. The supernatant was recovered and passed through a 0.45 μm filter. The supernatant from the above filter was loaded (maximum 50 mg of protein) on a gel filtration column (2.5×90 cm, ACA 34 LKB) with a flow rate of 0.3-0.4 ml/min, equilibrated with phosphate-buffered saline (PBS), 0.1% SDS. The fractions containing SOD-p31 were pooled and concentrated either by vacuum dialysis or using a YM5 Amicon membrane at 40 psi. The protein was stored at −20° C. as concentrated solution.

Gel electrophoresis analysis showed that the SOD-p31 protein migrates having a molecular weight of about 46 kd and is over 90% pure.

Similar constructions and results have been obtained by expressing an SOD-p31 fusion under regulation of a bacterial trp-lac promoter in *E. coli*.

The SOD-p31 fused protein finds use in immunoassays to detect the presence of antibodies against AIDS in body fluids. Successful results have been obtained using the SOD-p31 fusion protein in ELISA as well as in strip assays.

Example III: Construction and Expression of Expression Vectors for SOD-IGF-2 Fusion Protein.

A yeast expression plasmid pYLUIGF2-14, containing the human SOD gene fused to the amino terminus of the IGF2 gene (see EPO 123 228) was constructed. Expression of SOD-IGF2 is non-constitutive and it is under regulation of a hybrid ADH-GAP promoter.

Construction of pYLUIGF2-14

For the construction of a gene for a fused protein SOD-IGF2 to be expressed in yeast, plasmid pYS18 was used. Plasmid pYS18 contains the SOD gene fused to the proinsulin gene under the regulation of the ADH-GAP promoter and s-factor terminator (see Table 1). Plasmid pYS18 was digested with BamHI and EcoRI. The 1830 bp fragment (containing the ADH-GAP promoter and SOD gene) was purified by gel electrophoresis.

A second BamHI (460 bp) fragment coding for amino acid residues 41 to 201 of IGF-2 and for the α-factor terminator (see EPO 123 228) was ligated to the following linker:

```
EcoRI                                                              SalI
AATTCCATGGCTTACAGACCATCCGAAACCTTGTGTGGTGGTGAATTGG
      GGTACCGAATGTCTGGTAGGCTTTGGAACACACCACCACTTAACCAGCT
```

The linker provides for an EcoRI overhang, an ATG codon for methionine and for codons 1-40 of IGF2 and SalI overhang.

The resulting EcoRi-BamHI (510 bp) fragment containing the IGF-2 gene and α-factor terminator was ligated to the 1830 bp BamHI-EcoRI fragment containing the ADH-GAP promoter and SOD (see above). The resulting BamHI (2340 bp) fragment was cloned into BamHI digested and phosphatase treated pAB24 (see below) to yield pYLUIGF2-14.

pAB24 is a yeast expression vector (see FIG. 2) which contains the complete 2μ sequences (Broach 1981, In: *Molecular Biology of the Yeast Saccharomyces* 1:445, Cold Spring Harbor Press) and pBR322 sequences. It also contains the yeast URA3 gene derived from plasmid YEp24 (Botstein et al., 1979 Gene 8:17) and the yeast LEU2$^d$ gene derived from plasmid pC1/1 (see EPO 116201). Insertion of the expression cassette was in the BamHr site of pBR322, thus interrupting the gene for bacterial resistance to tetracycline.

Expression of SOD-IGF2

Yeast AB110 (Matα, ura3-52, leu2-04 or both leu2-3 and leu2-112, pep4-3, his4-580, cir°) was transformed with pYLUIGF2-14. Transformants were grown up on ura⁻selective plate. Transformant colonies were transferred to 3 ml leu⁻selective media and grown 24 hrs in 30° C. shaker. 100 μl of a $1 \times 10^{-4}$ dilution of this culture was plated onto ura⁻plates and individual transformants were grown up for ~48-72 hrs. Individual transformants were transferred to 3 ml leu media and grown 24 hrs in a 30° C. shaker. One ml each of these cultures was diluted into 24 ml UEP, 1% glucose media and cells were grown for 16-24 hours for maximum yield of SOD-IGF2. Cells were centrifuged and washed with $H_2O$. Cells were resuspended in 2-volumes of lysis buffer (phosphate buffer, pH 7.3 (50-100mM), 0.1% Triton X100). Two volumes of acid washed glass beads were added and the suspension was alternately vortexed or set on ice (5×, 1 min. each cycle). The suspension was centrifuged and the supernatant decanted. The insoluble pellet was incubated in lysis buffer 1% SDS at room temperature for 30 min. The suspension was centrifuged and the supernatant was frozen and lyophilized.

Two other constructions: pYLUIGF2-15 and pYUICF2-13 were used as controls for expression of a non-fused IGF2. The former plasmid (pYLUIGF2-15) for intracellular expression contains the IGF2 gene under control of the GAP promoter and a-factor terminator. The latter plasmid (pYUIGF2-13) for secretion of IGF2, the IGF-2 gene under control for the GAP promoter, s-factor leader and s-factor terminator.

EXPRESSION OF IGF2

| Construction in AB110 | PAGE STAIN (% of total cell protein) | RRA+ |
|---|---|---|
| 1. pYLUIGF2-15 ($GAP_p$IGF2.$af_t$) | NOT DETECTABLE | NA |
| 2. pYUIGF2-13 ($GAP_p\alpha f_L$.IGF2.$af_T$) | BARELY DETECTABLE | 10 μg/l |
| 3. pYLUIGF2-14 (ADH2/$GAP_p$SOD.IGF2.$af_T$) | 10-15% | NA* |

NA: Not available.
*By Coomassie blue staining, the SOD.IGF2 fusion protein represents 10-15% of the total cell protein, i.e., ~100-300 mg/l culture equivalent. IGF2 represents ~⅓ of the fusion protein, therefore it constitutes about 30-100 mg/l culture equivalent. Analytical CNBr cleavage reactions with the fusion protein have resulted in a band on PAGE which migrates to the position expected for IGF2.
+RRA-IGF2 levels were measured by a placental membrane radioreceptor assay (RRA) according to Horner et al., J. of Clinical Endocrinology and Metabolism (1978) 47:1287 and Marshall et al., J. of Clinical Endocrinology and Metabolism (1974) 39:283. Placental membranes for the RRA were prepared by the method of Cuatrecasas, Proc. Natl. Acad. Sci. USA (1972) 69:318.

Protocol for CNBr Cleavage of SOD.IGF2

The insoluble fraction from glass bead lysis of yeast cells was dissolved in 70% formic acid. CNBr crystals (μ/g CNBr/100 mg fusion protein) were added and incubation was carried out at room temperature for 12-15in the dark. This step may be repeated after 24 hrs if cleavage is incomplete.

It is evident from the above results that otherwise difficultly and inefficiently produced polypeptides may be produced in substantially enhanced yields by employing a fused protein, where the fusion protein includes a relatively short stable polypeptide sequence joined to the other polypeptide by a selectively cleavable site. Thus, high levels of the fusion protein are obtained in a eukaryotic host, such as yeast, allowing for the efficient production of desired polypeptides heterologous to the host.

Although the foregoing invention has been described in some detail by way of illustration and example for purposes of clarity of understanding, it will be obvious that certain changes and modifications may be practiced within the scope of the appended claims.

What is claimed is:

1. A fusion polypeptide consisting essentially of human copper zinc superoxide dismutase joined to a polypeptide having 15 to 300 amino acids.

2. The fusion polypeptide of claim 1, wherein the human superoxide dismutase is joined to said polypeptide having 15 to 300 amino acids by a selectively cleavable site or a link having one amino acid, wherein said link provides for a selectively cleavable site.

3. The fusion polypeptide of claim 2, wherein the human superoxide dismutase is joined to a mammalian polypeptide.

4. The fusion polypeptide of claim 3 wherein said link is (Asp)4Lys and said mammalian polypeptide is at least a portion of IGF-I or IGF-II.

5. The fusion polypeptide of claim 2, wherein the human superoxide dismutase is joined to a viral polypeptide.

6. A fusion polypeptide consisting essentially of human copper-zinc superoxide dismutase joined to a mammalian polypeptide having 15 to 300 amino acids.

7. The fusion polypeptide of claim 6 wherein said mammalian polypeptide is at least a portion of proinsulin.

8. An fusion polypeptide consisting essentially of human copper-zinc superoxide dismutase joined to a viral polypeptide having 15 to 300 amino acids.

9. The fusion polypeptide of claim 8, wherein said viral polypeptide is a polypeptide from an AIDS related virus.

* * * * *